United States Patent [19]
Patane et al.

[11] Patent Number: 5,661,163
[45] Date of Patent: *Aug. 26, 1997

[54] ALPHA-1A ADRENERGIC RECEPTOR ANTAGONISTS

[75] Inventors: Michael A. Patane, Harleysville; Mark G. Bock, Hatfield; Roger M. Freidinger, Lansdale; Rose Ann Ponticello, Harleysville, all of Pa.

[73] Assignee: Merck & Co., Inc., Rahway, N.J.

[*] Notice: The term of this patent shall not extend beyond the expiration date of Pat. No. 5,620,993.

[21] Appl. No.: 488,272

[22] Filed: Jun. 7, 1995

[51] Int. Cl.⁶ .................. A61K 31/445; C07D 211/36
[52] U.S. Cl. .................. 514/331; 514/330; 514/284; 546/215; 546/225
[58] Field of Search .................. 514/316, 318, 514/326, 327, 331, 330, 284; 546/194, 205, 206, 213, 214, 215, 221, 225

[56] References Cited

U.S. PATENT DOCUMENTS 5,403,847  4/1995  Gluchowski et al. .................. 514/318

FOREIGN PATENT DOCUMENTS

| 442 424 A1 | 8/1991 | European Pat. Off. |
| 1166364 | 10/1969 | United Kingdom. |
| 1206487 | 9/1970 | United Kingdom. |
| 94/08040 | 4/1994 | WIPO. |
| 94/10989 | 5/1994 | WIPO. |
| 94/21660 | 9/1994 | WIPO. |
| 94/22829 | 10/1994 | WIPO. |
| 95/07075 | 3/1995 | WIPO. |

OTHER PUBLICATIONS

J. Med. Chem., Wetzel et al., Discovery of Alpha 1a Adrenergic Receptor Antagonists Based on the L–Type Ca2+ Channel Antagonist Niguldipine, May 12, 1995, vol. 38, No. 10, pp. 1579–1581.

*Primary Examiner*—C. Warren Ivy
*Assistant Examiner*—Garth Dahlen
*Attorney, Agent, or Firm*—Mary A. Appollina; Melvin Winokur

[57] ABSTRACT

This invention relates to certain novel compounds and derivatives thereof, their synthesis, and their use as selective alpha-1a adrenergic receptor antagonists. One application of these compounds is in the treatment of benign prostatic hyperplasia. These compounds are selective in their ability to relax smooth muscle tissue enriched in the alpha 1a receptor subtype without at the same time inducing orthostatic hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia are achieved.

22 Claims, No Drawings

ALPHA-1A ADRENERGIC RECEPTOR ANTAGONISTS

FIELD OF THE INVENTION

This invention relates to certain novel compounds and derivatives thereof, their synthesis, and their use as selective alpha-1a adrenoceptor antagonists. More particularly, the compounds of the present invention are useful for treating benign prostatic hyperplasia (BPH).

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in WO 92/0073, the selective ability of the R(+) enantiomer of terazosin to selectively bind to adrenergic receptors of the alpha 1 subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, is limited by their $\alpha_2$ adrenergic receptor mediated induction of increased plasma catecholamine concentration and the attendant physiological sequelae (increased heart rate and smooth muscle contraction).

For a general background on the $\alpha$-adrenergic receptors, the reader's attention is directed to Robert R. Ruffolo, Jr., $\alpha$-*Adrenoreceptors: Molecular Biology, Biochemistry and Pharmacology*, (*Progress in Basic and Clinical Pharmacology* series, Karger, 1991), wherein the basis of $\alpha_1/\alpha_2$ subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting $\alpha$-adrenergic receptor affinity was explored.

The cloning, sequencing and expression of alpha receptor subtypes from animal tissues has led to the subclassification of the receptors into $\alpha_{1a}$, (Lomasney, et at., *J. Biol. Chem.*, 266:6365–6369 (1991), rat $\alpha_{1a}$; Bruno et al., *BBRC*, 179:1485–1490 (1991), human $\alpha_{1a}$), $\alpha_{1b}$ (Cotecchia, et al., *PNAS*, 85;7159–7163 (1988), hamster $\alpha 1_b$; Libert, et al., *Science*, (1989), dog $\alpha_{1b}$; Ramarao, et al., *J. Biol. Chem.*, 267:21936–21945 (1992), human $\alpha_{1b}$), and most recently, in a study using bovine brain, a new $\alpha_{1c}$ subtype was proposed (Schwinn, et al., *J. Biol. Chem.*, 265:8183–8189 (1990); Hirasawa et al., *BBRC*. 195:902–909 (1993), described the cloning, functional expression and tissue distribution of a human $\alpha_{1c}$ adrenergic receptor; Hoehe et al., *Human Mol. Genetics* 1(5):349 (8/92) noted the existence of a two-allele Pst1 restriction fragment polymorphism in the $\alpha_{1c}$ adrenergic receptor gene; another study suggests that there may even be an alpha-1d receptor subtype, see Perez et al., *Mol. Pharm.*, 40:876–883, 1992). Each $\alpha_1$ receptor subtype exhibits its own pharmacologic and tissue specificities. Schwinn and coworkers noted that the cloned bovine $\alpha_{1c}$ receptor exhibited pharmacological properties proposed for the $\alpha_{1a}$ subtype. Nonetheless, based on its non-expression in tissues where the $\alpha_{1a}$ subtype is expressed, and its sensitivity to chloroethylclonidine, the receptor was given a new designation.

The differences in the $\alpha$-adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra.

In benign prostatic hyperplasia, the male hormone 5$\alpha$-dihydrotestosterone has been identified as the principal culprit. The continual production of 5$\alpha$-dihydrotestosterone by the male testes induces incremental growth of the prostate glad throughout the life of the male. Beyond the age of about fifty years, in many men, this enlarged glad begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.s' product PROSCAR® (finasteride). The effect of this compound is to inhibit the enzyme testosterone 5-alpha reductase, which converts testosterone into 5$\alpha$-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not mediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the urethral smooth muscle, by binding to alpha-1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/0073, the selective ability of the R(+) enantiomer of terazosin to bind to adrenergic receptors of the $\alpha_1$ subtype was reported. In addition, in WO 92/161213, hereby incorporated by reference, combinations of 5-alpha-reductase inhibitory compounds and alpha 1-adrenergic receptor blockers (terazosin, doxazosin, prazosin, bunazosin, indoramin, alfuzosin) were disclosed. However, no information as to the $\alpha_{1a}$, $\alpha_{1b}$, or $\alpha_{1c}$ subtype specificity of these compounds was provided as this data and its relevancy to the treatment of BPH was not known. Current therapy for BPH uses existing non-selective alpha-1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha-1a and alpha-1b receptors in the peripheral vasculature, e.g., orthostatic hypotension and syncope.

Typically, identification of active compounds is accomplished through use of animal tissues known to be enriched in adrenergic receptors. Thus, rat tissues have been used to screen for potential adrenergic receptor antagonists. However, because of species variability, compounds which appear active in animal tissue may not be active or sufficiently selective in humans. This results in substantial wastage of time and effort, particularly where high volume compound screening programs are employed. There is also the danger that compounds, which might be highly effective in humans, would be missed because of their absence of appreciable affinity for the heterologous animal receptors. In this regard, it has been noted that even single amino acid changes between the sequence of biologically active proteins in one species may give rise to substantial pharmacological differences. Thus, Fong et al., (*J. Biol. Chem.*, 267:25668–25671, 1992) showed that there are 22 divergent amino acid residues between the sequence of the human neurokinin-1 receptor and the homologous rat receptor. They further showed, in studies with mutant receptors, that substitution of only two amino acid residues was both necessary and sufficient to reproduce the rat receptor's antagonist binding affinity in the human receptor. Oksenberg et al., (*Nature*, 360:161–163, 1992) showed that a single amino-acid difference confers major pharmacological variation between the human and the rodent 5-hydroxytryptamine receptors. Likewise, Kuhse et al., (*Neuron*, 5:867–873, 1990) showed that a single amino-acid exchange alters the pharmacology of the neonatal rat glycine receptor subunit. This difficulty and unpredictability has resulted in a need for a compound screen which will identify compounds that will be active in humans.

These problems were solved by cloning the human adrenergic receptor of the $\alpha_{1c}$ subtype (ATCC CRL 11140) and the use of a screening assay which enables identification of compounds which specifically interact with the human $\alpha 1c$ adrenergic receptor. [PCT International Application Publication Nos. WO94/08040, published 14 Apr. 1994 and WO94/10989, published 26 May 1994] As disclosed in the instant patent disclosure, a cloned human $\alpha_{1c}$ adrenergic receptor and a method for identifying compounds which bind the human $\alpha_{1c}$ receptor has now made possible the identification of selective human $\alpha_{1c}$ adrenergic receptor antagonists useful for treating BPH. The instant patent disclosure discloses novel compounds which selectively bind to the human $\alpha_{1c}$ receptor. These compounds are further tested for binding to other human alpha 1 receptor subtypes, as well as counterscreened against other types of receptors, thus defining the specificity of the compounds of the present invention for the human $\alpha_{1c}$ adrenergic receptor.

Compounds of this invention are used to reduce the acute symptoms of BPH. Thus, compounds of this invention may be used alone or in conjunction with a more long-term anti-BPH therapeutics, such as testosterone 5-alpha reductase inhibitors, including PROSCAR® (finasteride). Aside from their utility as anti-BPH agents, these compounds may be used to induce highly tissue-specific, localized $\alpha_{1c}$ adrenergic receptor blockade whenever this is desired. Effects of this blockade include reduction of intra-ocular pressure, control of cardiac arrhythmias, and possibly a host of alpha-1c receptor mediated central nervous system events.

NOMENCLATURE

Recently, a new $\alpha_1$ adrenergic receptor ($\alpha_1$-AR) classification scheme similar to that proposed by Ford, et al. [$\alpha_1$-*Adrenoceptor Classification: Sharpening Occam's Razor, Trends in Pharm. Sci.* 1994, 15, 167–170] was adopted at the August, 1994 meeting of the International Union of Pharmacology (IUPHAR) in Montreal, Canada. The $\alpha_1$-AR genes formerly known as $\alpha_{1a/d}$, $\alpha_{1b}$ and $\alpha_{1c}$ were renamed $\alpha_{1d}$, $\alpha_{1b}$ and $\alpha_{1a}$, respectively. This new naming system reflects the correspondence between the proteins encoded by the $\alpha_{1a}$ and $\alpha_{1b}$ genes (new IUPHAR nomenclature) and the receptors characterized by traditional pharmacological means as $\alpha_{1A}$ and $\alpha_{1B}$, respectively, in the literature. Recombinant receptors and receptors characterized pharmacologically in tissues are distinguished by lowercase and uppercase subscripts, respectively.

The above discussion contained in the Background section used the former classification scheme (i.e., $\alpha_{1a/d}$, $\alpha_{1b}$ and $\alpha_{1c}$); however, hereinafter, the new classification scheme will be utilized (i.e., $\alpha_{1d}$, $\alpha_{1b}$ and $\alpha_{1a}$). Thus, what was formerly referred to as the $\alpha_{1c}$ receptor (and $\alpha_{1c}$ receptor antagonists) will hereinafter be referred to utilizing the new nomenclature as the $\alpha_{1a}$ receptor (and $\alpha_{1a}$ receptor antagonists).

SUMMARY OF THE INVENTION

The present invention provides compounds for the treatment of urinary obstruction caused by benign prostatic hyperplasia (BPH). The compounds selectively antagonize the human alpha-1a adrenergic receptor at nanomolar and subnanomolar concentrations while exhibiting at least ten fold lower affinity for the alpha-1d and alpha-1b human adrenergic receptors and many other G-protein coupled receptors. This invention has the advantage over non-selective alpha-1 adrenoceptor antagonists of reduced side effects related to peripheral adrenergic blockade. Such side effects include orthostatic hypotension, syncope, lethargy, etc. The compounds of the present invention have the structure:

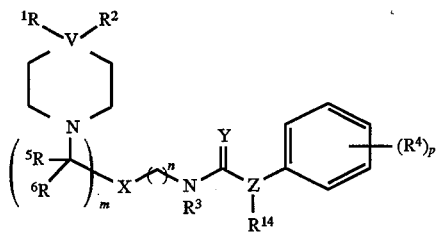

wherein

V is selected from carbon or nitrogen, provided that when V is nitrogen, then $R^2$ is absent;

X is selected from $CH_2$, $CHOR^5$, CHF, $CHR^5$, $CR^5R^6$, $CF_2$, $CHCHF_2$, $C=CF_2$ or C=O;

Y is selected from oxygen, $NR^8$ or sulfur;

Z is selected from CH, $CCO_2R^5$, $CH(CH_2)_qCO_2(R^5)_2$, $COR^{12}$, $CNR^{12}R^{13}$, $CHOR^{12}$, $CHNR^{12}R^{13}$ or $C(CH_2)_qCN(R^5)_2$;

$R^1$ is selected from unsubstituted, mono- or poly-substituted phenyl where the substitutents on the phenyl are independently selected from halogen, cyano, $CO_2R^5$, $OR^5$, $(CH_2)_qCON(R^5)_2$, $(CH_2)_qCO_2R^5$ or $C_{1-4}$ alkyl; or unsubstituted, mono- or poly-substituted: pyridyl, thiophenyl, furanyl or naphthyl where the substituents on the pyridyl, thiophenyl, furanyl or naphthyl are independently selected from $CF_3$, phenyl, $OR^5$, halogen, $C_{1-4}$ alkyl or $C_{3-8}$ cycloalkyl;

$R^2$ is selected from hydrogen, cyano, $CO_2R^5$, $CON(R^5)_2$, tetrazole or isooxadiazole;

$R^3$ is selected from hydrogen, cyano, $CO_2R^5$, $CON(R^5)_2$, $C_{1-8}$ alkyl, $C_{3-8}$ cycloalkyl or $(CH_2)_qCO_2R^5$;

$R^4$ is selected from hydrogen, $OR^5$, $C_{1-8}$ alkyl or halogen;

$R^5$ and $R^6$ are each independently selected from hydrogen, $C_{1-8}$ alkyl, $C_{3-8}$ cycloalkyl, halogen substituted $C_{1-4}$ alkyl and halogen substituted $C_{3-8}$ cycloalkyl;

$R^8$ is selected from hydrogen, cyano or $SO_2R^5$;

$R^{12}$ and $R^{13}$ are each independently selected from hydrogen, $C_{1-8}$ alkyl, $C_{3-8}$ cycloalkyl, CHO, $COR^5$, $CONR^5R^6$, $(CH_2)_qOR^5$, $R^{14}$ is selected from hydrogen, $C_{1-8}$ alkyl, $C_{3-8}$ cycloalkyl, $C_{1-4}$ alkoxy, morpholinyl, piperazinyl, δ-valerolactamyl, 2-pyrrolidonyl, thiophenyl, furanyl, pyridinyl, naphthyl or unsubstituted, mono- or poly-substituted phenyl where the substituents on the phenyl are independently selected from $C_{1-4}$ alkyl, $OR^5$ or halogen;

m, n and q are each independently an integer of from zero to three, provided that when m and n are both zero, then X is selected from $CH_2$, CHF, $CHR^5$, $CR^5R^6$, $CF_2$, $CHCHF_2$, $C=CF_2$ or $C=O$; and p is an integer of from zero to five;

and the pharmaceutically acceptable salts thereof.

In one embodiment of the invention is the compound of the formula

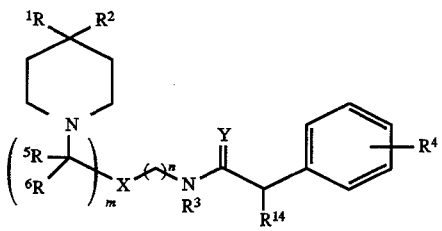

wherein $R^1$ is selected from unsubstituted, mono- or poly-substituted phenyl where the substitutents on the phenyl are independently selected from halogen, cyano, $CO_2R^5$, $OR^5$, $CON(R^5)_2$ or $C_{1-4}$ alkyl; pyridyl; thiophenyl; furanyl; or unsubstituted, mono- or poly-substituted naphthyl where the substituent on the naphthyl are independently selected from $CF_3$, phenyl, $OR^5$, halogen, $C_{1-4}$ alkyl or $C_{3-8}$ cycloalkyl; and where all other variables are as defined above;

and the pharmaceutically acceptable salts thereof.

In a class of the invention are the compounds of the formula

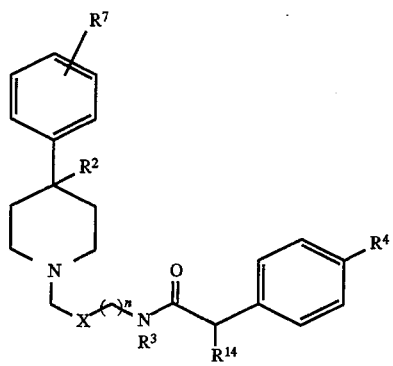

wherein $R^2$ is selected from cyano or $CO_2R^5$;

$R^4$ is selected from hydrogen, halogen or $C_{1-4}$ alkyl;

$R^7$ is selected from hydrogen, $CF_3$, cyano, halogen or $C_{1-4}$ alkyl;

$R^{14}$ is selected from hydrogen, $C_{1-8}$ alkyl, $C_{3-8}$ cycloalkyl or unsubstituted, mono- or poly-substituted phenyl where the substitutent on the phenyl are independently selected from halogen or $C_{1-4}$ alkyl; and where all other variables are as defined above;

and the pharmaceutically acceptable salts thereof.

In a subclass are the compounds of the formula

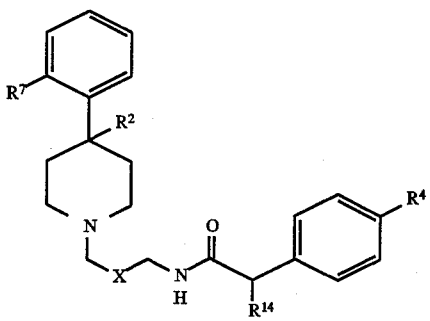

wherein $R^5$ is $C_{1-4}$ alkyl;

$R^{14}$ is selected from $C_{3-8}$ cycloalkyl or unsubstituted or mono-substituted phenyl wherein the substituent is selected from halogen or $C_{1-4}$ alkyl; and where all other variables are as defined above;

and the pharmaceutically acceptable salts thereof.

Illustrative of the invention are the compounds wherein X is selected from $CH_2$, CHOH or $C=O$;

$R^2$ is selected from cyano or $CO_2CH_3$;

$R^4$ is selected from hydrogen, chloro or methyl;

$R^7$ is selected from hydrogen, chloro or methyl; and $R^{14}$ is selected from cyclopentyl, cyclohexyl, phenyl, p-tolyl or p-chlorophenyl;

and the pharmaceutically acceptable salts thereof.

Illustrating the invention is the compound selected from 2,2-Bis(4-chlorophenyl)-N-[3-(4-cyano-4-phenylpiperidin-1-yl)propylacetamide;

2,2-Bis(4-chlorophenyl)-N-[3-(4-cyano-4-{2-methylphenyl}piperidin-1-yl)propyl]acetamide;

2,2-Bis(4-chlorophenyl)-N-[3-(4-{2-chlorophenyl}4-cyanopiperidin-1-yl)propylacetamide;

2,2-Bis(4-methylphenyl)-N-[3-(4-cyano-4-phenylpiperidin-1-yl)propyl]acetamide hydrochloride;

2,2-Bis(4-methylphenyl)-N-[3-({4-carboxymethyl}4-phenylpiperidin-1-yl)propyl]acetamide hydrochloride;

2,2-Bis(4-methylphenyl)-N-[3-(4-cyano-4-{2-methylphenyl}piperidin-1-yl)propyl]acetamide;

2,2-Bis(4-methylphenyl)-N-[3-(4-{2-chlorophenyl}4-cyanopiperidine-1-yl)propyl]acetamide;

2,2-Bis(4-methylphenyl)-N-[3-(4-cyano-4-phenylpiperidin-1-yl)2-hydroxypropyl]acetamide;

2,2-Bis(4-methylphenyl)-N-[3-(4-cyano-4-{2-methylphenyl}piperidin-1yl)2-hydroxypropyl]acetamide;

2,2-Bis(4-methylphenyl)-N-[3-(4-cyano-4-phenylpiperidine-1-yl)2-oxopropyl]acetamide;

2,2-Bis(4-methylphenyl)-N-[3-(4-cyano-4-{2-methylphenyl}piperidin-1-yl)2-oxopropyl]acetamide; or 2,2-Bis(4-methylphenyl)-N-[3-{4-(2-benzamido)piperizin-1-yl}propyl]acetamide;

and the pharmaceutically acceptable salts thereof.

An illustration of the invention is a pharmaceutical composition comprising a therapeutically effective mount of any of the compounds described above and a pharmaceutically acceptable carrier.

Exemplifying the invention is the composition further comprising a therapeutically effective mount of a testosterone 5-alpha reductase inhibitor. Preferably, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor) or a dual type 1 and type 2 testosterone 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

More specifically illustrating the invention is a method of treating benign prostatic hyperplasia in a subject in need thereof which comprises administering to the subject a therapeutically effective amount of any of the pharmaceutical compositions described above.

An example of the invention is a method of treating benign prostatic hyperplasia in a subject in need thereof which comprises administering to the subject a therapeutically effective amount of any of the compounds described above.

Further exemplifying the invention is the method of treating BPH wherein the compound additionally does not cause a fall in blood pressure at dosages effective to alleviate BPH.

Another illustration of the invention is the method of treating benign prostatic hyperplasia wherein the compound is administered in combination with a testosterone 5-alpha reductase inhibitor. Preferably, the testosterone 5-alpha reductase inhibitor is finasteride.

Further illustrating the invention is a method of inhibiting contraction of prostate tissue in a subject in need thereof which comprises administering to the subject a therapeutically effective amount of any of the compounds (or any of the compositions) described above.

More specifically exemplifying the invention is the method of inhibiting contraction of prostate tissue wherein the compound (or composition) additionally does not cause a fall in blood pressures at dosages effective to inhibit contraction of prostate tissue.

More particularly illustrating the invention is the method of inhibiting contraction of prostate tissue wherein the compound (or composition) is administered in combination with a testosterone 5-alpha reductase inhibitor; preferably, the testosterone 5-alpha reductase inhibitor is finasteride.

More particularly exemplifying the invention is a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain and cardiac arrhythmia.

DETAILED DESCRIPTION OF THE INVENTION

Representative compounds of the present invention exhibit high selectivity for the human alpha 1a adrenergic receptor. One implication of this selectivity is that these compounds display selectivity for lowering intraurethral pressure without substantially affecting diastolic blood pressure.

Representative compounds of this invention display submicromolar affinity for the human alpha 1a adrenergic receptor subtype while displaying at least ten-fold lower affinity for the human alpha 1d and alpha 1b adrenergic receptor subtypes, and many other G-protein coupled human receptors. Particular representative compounds of this invention exhibit nanomolar and subnanomolar affinity for the human alpha 1a adrenergic receptor subtype while displaying at least 30 fold lower affinity for the human alpha 1d and alpha 1b adrenergic receptor subtypes, and many other G-protein coupled human receptors. Preferred compounds of this invention exhibit Ki's for human alpha 1a adrenergic receptors which are more than 400 fold lower than for the human alpha 1d or alpha 1b adrenergic receptors, while exhibiting greater than 500 fold selectivity for the human alpha 1a adrenergic receptor over all other human G-protein coupled receptors tested (including serotonin, dopamine, alpha 2 adrenergic, beta adrenergic or muscarinic receptors).

These compounds are administered in dosages effective to antagonize the alpha 1a receptor where such treatment is needed, as in BPH. For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

The present invention includes within its scope prodrugs of the compounds of this invention. In general, such prodrugs will be functional derivatives of the compounds of this invention which are readily convertible in vivo into the required compound. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "aryl" as used herein, except where otherwise specifically defined, refers to unsubstituted, mono- or poly-substituted aromatic groups such as phenyl or naphthyl.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "substituted" shall be deemed to include multiple degrees of substitution by a named substitutent. The term "poly-substituted" as used herein shall include di-, tri-, tetra- and penta-substitution by a named substituent.

Where multiple substituent moieties are disclosed or claimed, the substituted compound can be independently substituted by one or more of the disclosed or claimed substituent moieties, singly or plurally.

The term heterocycle or heterocyclic ring, as used herein, represents an unsubstituted or substituted stable 5- to 7-membered monocyclic ring system which may be saturated or unsaturated, and which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl (i.e., thiophenyl), pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The term "thiophenyl," as used herein, refers to the group

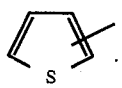

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The specificity of binding of compounds showing affinity for the $\alpha_{1a}$ receptor is shown by comparing affinity to membranes obtained from tranfected cell lines that express the $\alpha_{1a}$ receptor and membranes from cell lines or tissues known to express other types of alpha (e.g., $\alpha_{1d}$, $\alpha_{1b}$) or beta adrenergic receptors. Expression of the cloned human $\alpha_{1d}$, $\alpha_{1b}$, and $\alpha_{1a}$ receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting orthostatic hypotensive effects.

The ability of compounds of the present invention to specifically bind to the $\alpha_{1a}$ receptor makes them useful for the treatment of BPH. The specificity of binding of compounds showing affinity for the $\alpha_{1a}$ receptor is compared against the binding affinities to other types of alpha or beta adrenergic receptors. The human alpha adrenergic receptor of the 1-a subtype was recently identified, cloned and expressed as described in PCT International Application Publication Nos. WO94/08040, published 14 Apr. 1994 and WO 94/21660, published 29 Sep. 1994, each of which is hereby incorporated by reference. The cloned human $\alpha_{1a}$ receptor, when expressed in mammalian cell lines, is used to discover ligands that bind to the receptor and alter its function. Expression of the cloned human $\alpha_{1d}$, $\alpha_{1b}$, and $\alpha_{1a}$ receptors and comparison of their binding properties with known selective antagonists provides a rational way for selection of compounds and discovery of new compounds with predictable pharmacological activities.

Compounds of this invention exhibiting selective human $\alpha_{1a}$ adrenergic receptor antagonism may further be defined by counterscreening. This is accomplished according to methods known in the art using other receptors responsible for mediating diverse biological functions. [See e.g., PCT International Application Publication No. WO94/10989, published 26 May 1994; U.S. Pat. No. 5,403,847, issued Apr. 4, 1995]. Compounds which are both selective amongst the various human alpha 1 adrenergic receptor subtypes and which have low affinity for other receptors, such as the alpha2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha1a adrenergic receptors can be administered in a wide variety of therapeutic dosage forms in conventional vehicles for systemic administration. For example, the compounds can be administered in such oral dosage forms as tablets; capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. An effective amount of the drug is ordinarily supplied at a dosage level of from about 0.0002 mg/kg to about 250 mg/kg of body weight per day. Preferably, the range is from about 0.001 to 100 mg/kg of body weight per day, and especially from about 0.001 mg/kg to 7 mg/kg of body weight per day. The compounds may be administered on a regimen of 1 to 4 times per day.

Compounds of this patent disclosure may be used alone at appropriate dosages defined by routine testing in order to obtain optimal antagonism of the human α1a adrenergic receptor while minimizing any potential toxicity. In addition, co-administration or sequential administration of other agents which alleviate the effects of BPH is desirable. Thus, in one embodiment, this includes administration of compounds of this invention and a human testosterone 5-α reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example, hereby incorporated by reference). In addition to PROSCAR®, which is principally active in prostatic tissue due to its selectivity for human 5-α reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5α-reductase inhibitors have been described in WO93/23420, EP 0572166; WO 93/23050; WO93/23038, ;WO93/23048; WO93/23041; WO93/23040; WO93/23039; WO93/23376; WO93/23419, EP 0572165; WO93/23051, each of which is hereby incorporated by reference.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject is about 0.01 mg per subject per day to about 50 mg per subject per day in combination with an $\alpha_{1a}$ antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, compounds of this invention exhibiting alpha 1a adrenergic receptor blockade can be combined with a therapeutically effective amount of a 5α-reductase 2 inhibitor, such as finasteride, in addition to a 5α-reductase 1 inhibitor, such as 4,7β-dimethyl-4-aza-5α-cholestan-3-one, in a single oral, systemic, or parenteral pharmaceutical dosage formulation. Alternatively, a combined therapy can be employed wherein the alpha 1a adrenergic receptor antagonist and the 5α-reductase 1 or 2 inhibitor are administered in separate oral, systemic, or parenteral dosage formulations. See, e.g., U.S. Pat. Nos. 4,377,584 and 4,760,071 which describe dosages and formulations for 5α-reductase inhibitors.

Abbreviations used in the instant specification, particularly the Schemes and Examples, are as follows:
Boc or BOC=t-butyloxycarbonyl
BOPCl=bis(2-oxo-3-oxazolidinyl)phosphinic chloride
Cbz-Cl=benzyloxycarbonyl chloride
DAST=diethylaminosulfurtrifluofide
DEAD=diethylazodicarboxylate
DMF=N,N-dimethylformamide
EDCI=1-(3-dimethylaminopropyl)-3-ethylcarbodimide hydrochloride
Et=ethyl
$Et_3N$=triethylamine
EtOAc=ethyl acetate
EtOH=ethanol
FABLRMS=fast atom bombardment low resolution mass spectroscopy
HPLC=high performance liquid chromatography
HOAc=acetic acid
HOBt=1-hydroxy benzotriazole hydrate
i-PrOH=2-propanol
i-$Pr_2$NEt=diisopropylethylamine
Me=methyl
MeOH=methanol
NMR=nuclear magnetic resonance
PCTLC=preparative centrifugal thin layer chromatography
PEI=polyethylenimine
Ph=phenyl
RT=retention time
TFA=trifluoroacetic acid
THF=tetrahydrofuran
TLC=thin layer chromatography The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Unless otherwise indicated, all variables are as defined above.

The preparation of 4,4-disubstituted piperidines 4 was accomplished via spiro annulation of substituted acetonitrile derivatives 1 with N-Boc bischloroethyl amine under basic conditions in good yields. The resulting nitriles could then be hydrolyzed and further elaborated or simply deprotected providing 4 and alkylated with N-Boc bromopropyl amine 5 (m=1) or bromoethyl amine (m=0) producing 6. Subsequent N-Boc deprotection afforded 7 and coupling with acetic acids or acetic acid chlorides derivatives 8a–k produced the desired amides 9a–k in modular fashion. Alternatively, the piperidine 4 was alkylated with the bromoalkyl amides 10a–k, which were prepared via coupling of the acetic acid derivatives 8a–k to bromopropyl or bromoethyl amine prior to alkylation.

SCHEME 1

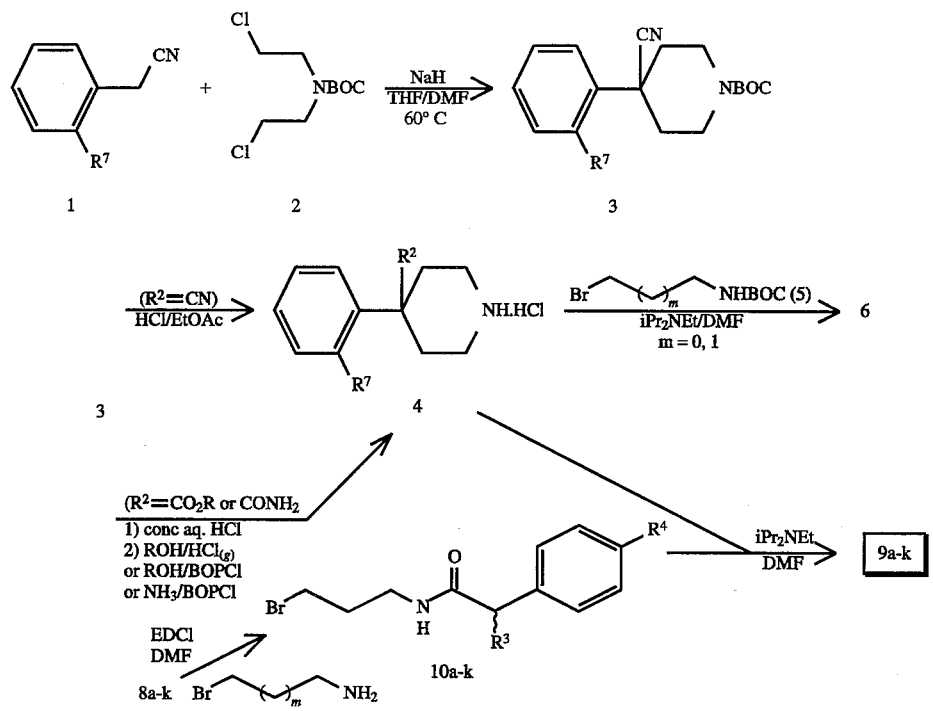

-continued
SCHEME 1

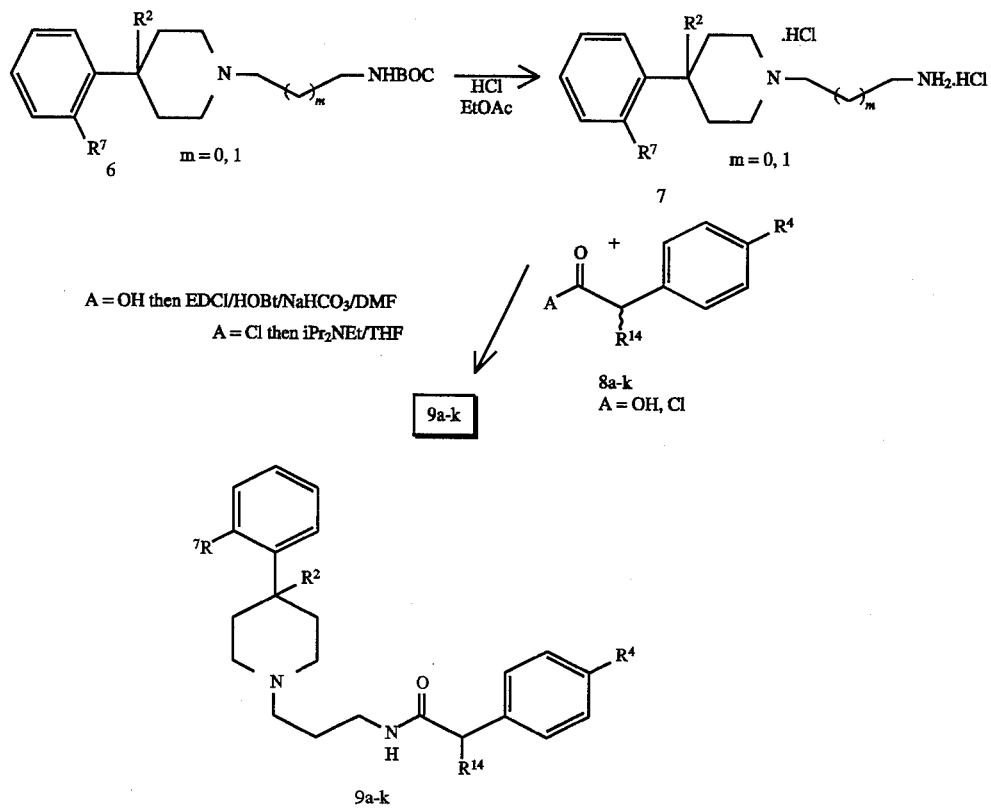

A = OH then EDCl/HOBt/NaHCO₃/DMF
A = Cl then iPr₂NEt/THF

| 9a-k | R⁴ | R⁷ | R² | R¹⁴ |
|---|---|---|---|---|
| 9a | Me | H | CO₂Me | p-tolyl |
| 9b | Me | H | CN | p-tolyl |
| 9c | H | H | CO₂Me | Ph |
| 9d(±) | H | H | CO₂Me | cyclohex |
| 9e(±) | H | H | CN | cyclopent |
| 9f | Cl | H | CO₂Me | p-Cl—Ph |
| 9g | Cl | H | CN | p-Cl—Ph |
| 9h | Me | Me | CN | p-tolyl |
| 9i | Me | Cl | CN | p-tolyl |
| 9k | Cl | Cl | CN | p-Cl—Ph |

The synthesis of compounds similar to 9a–k, however bearing additional structural elements along the three carbon tether was accomplished as outlined in Scheme 2. Starting with the previously described piperidines 4, whose reaction with N-(2,3-epoxypropyl)phthalimide produced the hydroxy phthalimide (±)-10 which was subsequently deprotected in the presence of anhydrous hydrazine providing (±)-11, and coupled to a variety of acetic acid derivatives 8 supplying 12a,b. These hydroxy containing phenyl acetic acetamides were oxidized under Swern conditions to the corresponding keto derivatives 13a,b. Intrinsically useful in this strategy is the capabilities for further functionalization utilizing both the hydroxy or keto groups. Compounds such as 12 can be electrophilic substrates for a plethora of nucleophiles under Mitsunobu conditions 14. While ketones such as 13 can, for instance, be olefinated and subsequently reduced 15.

SCHEME 2

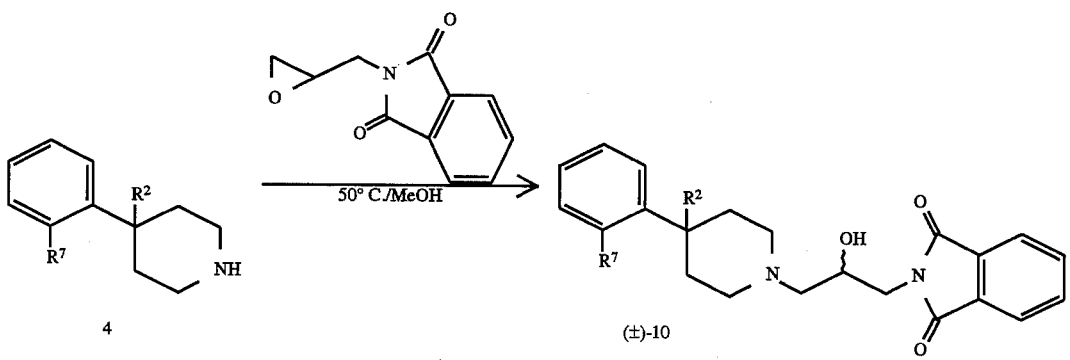

-continued
SCHEME 2
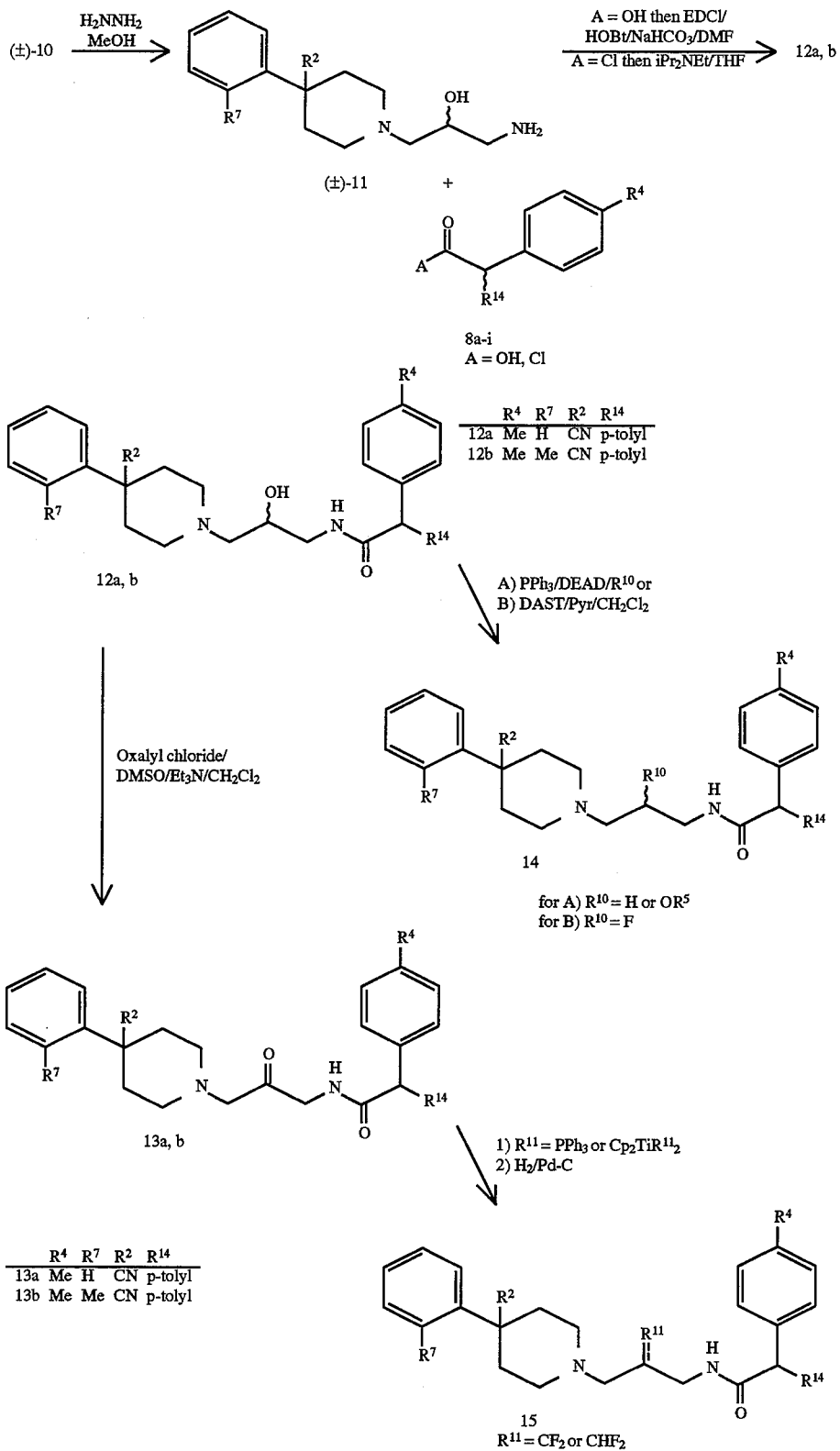

The following examples are provided to further define the invention without, however, limiting the invention to the particulars of these examples.

EXAMPLE 1

Bis(2-chloroethyl)-N-(1,1-dimethylethoxy)carbonyl Amine

A solution of N-(2,2'-bischloro)diethyl amine (23.0 g, 0.130 mol) and di-tert-butyl dicarbonate (28.8 g, 0.130 mol) in $CH_2Cl_2$ (150 mL) was treated with N,N-diisopropylethylamine (22.52 ml, 0.720 mol) at room temperature (1.5 h). The solvent was removed in vacuo and the residue was triturated with ether (300 ml). The ether solution was collected and concentrated in vacuo affording N-(2,2'-bischloro)diethyl-N-(1,1-dimethylethoxy)carbonyl amine as a clear oil.

$^1$H NMR ($CDCl_3$, 400 MHz) d 3.65 (m, 8H), 1.52 (s, 9H)

FABLRMS (3:1 mixture of dithiothreitol and dithioerythritol in MeOH) m/e 242 g/mole ($M^++H$, $C_{25}H_{29}N_2O_5SCl$= 242.2 g/mole.)

EXAMPLE 2

4-Cyano-N-(1,1-dimethylethoxy)carbonyl-4-(2-methylphenyl) piperidine

A solution of bis(2-chloroethyl)-N-(1,1-dimethylethoxy)carbonyl amine (1.438 g, 5.94 mmol) and 2-methylphenyl acetonitrile (600 mg, 3.96 mmol) in a 4:1 mixture of THF/DMF (15 mL) was treated with NaH (357.9 mg, 8.7 mmol) at 60° C. (3 d). The solvent was removed in vacuo, the residue dissolved in EtOAc (200 ml) and washed with saturated $NaHCO_3$ (50 ml), $H_2O$ (2×50 ml), and saturated aqueous NaCl (50 ml), dried ($Na_2SO_4$) and concentrated in vacuo. PCTLC ($SiO_2$, 6 mm, 100% hexane) afforded 4-cyano-N-(1,1-dimethylethoxy)carbonyl-4-(2-methylphenyl) piperidine as a yellow/orange oil.

$^1$H NMR ($CDCl_3$, 400 MHz) d 7.25 (m,4H), 4.28 (br s, 2H), 3.28 (br t, 2H), 2.65 (s, 3H), 2.32 (d, 2H, J=13.0 Hz), 2.32 (dt 2H, J=4.1, 13.0 Hz), 1.48 (s, 9H).

HPLC (Vydac; C18; diameter=4.6 mm; length=15 cm; gradient=$CH_3CN$ [0.1% TFA]-$H_2O$ [0.1% TFA], 5%–95%, 95–5% over 20 min. 1.5 ml/min flow rate; RT=11.730 min; focus=215 nm; 75% pure.

EXAMPLE 3

4-Cyano-4-(2-methylphenyl)piperidine Hydrochloride

A solution of EtOAc saturated with HCl (200 ml) was added to 4-cyano-N-(1,1-dimethylethoxy)carbonyl-4-(2-methylphenyl)piperidine (31 mg, 0.097 mmol). The resulting mixture was allowed to react for 1 hour at room temperature. The EtOAc was removed in vacuo affording 4-cyano-4-(2-methylphenyl)piperidine hydrochloride as a white solid.

$^1$H NMR ($CD_3OD$, 400 MHz) d 7.37 (m, 1H), 7.32 (m, 3H), 3.64 (dd, 2H, J=2.2, 11.4 Hz), 3.46 (t , 2H, J=13.5 Hz), 2.64 (m, 2H), 2.65 (s, 3H), 2.28 (t d, 2H, J=3.7 Hz, 13.5 Hz).

FABLRMS (3:1 mixture of dithiothreitol and dithioerythritol in MeOH) m/e 201 g/mole ($M^++H$, C13H16N2=201.3 g/mole.)

HPLC (Vydac; C18; diameter=4.6 mm; length=15 cm; gradient=$CH_3CN$ [0.1% TFA]-$H_2O$ [0.1% TFA], 5%–95%, 95–5% over 20 min. 1.5 ml/min flow rate; RT=5.82 min; focus=215 nm; 100% pure.

Anal. Calcd for $C_{13}H_{16}N_2$. HCl and 0.30 $H_2O$ and 0.25 $CH_2Cl_2$: C=60.42, H=6.93, N=10.64. Found: C=60.37, H=6.83, N=11.09.

EXAMPLE 4

4-(2-Chlorophenyl)-4-cyano-N-(1,1-dimethylethoxycarbonyl)piperidine

A solution of bis(2-chloroethyl)-N-(1,1-dimethylethoxy)carbonyl amine (9.298 g, 38.4 mmol) and 2-chlorophenylacetonitrile (5.0 g, 32.0 mmol) in a 4:1 mixture of THF/DMF (15 mL) was treated with NaH (2.82 g, 70.4 mmol) at 60° C. (7 d). The solvent was removed in vacuo, the residue dissolved in EtOAc (200 ml) and washed with saturated $NaHCO_3$ (50 ml), $H_2O$ (2×50 ml), and saturated aqueous NaCl (50 ml), dried ($Na_2SO_4$) and concentrated in vacuo. Trituration of the residue with 100% MeOH afforded 4-(2-chlorophenyl)-4-cyano-N-(1,1-dimethylethoxy) carbonyl piperidine as a white solid.

$^1$H NMR ($CD_3OD$, 400 MHz) d 7.53 (m, 2H), d 7.41 (m, 2H), 4.28 (br dd, 2H, J=13.4 Hz), 3.26 (m, 2H), 2.52 (dd, 2H, J=2.2, 11.2 Hz), 2.03 (dt, 2H, J=4.0, 9.2 Hz), 2.03 (s, 9H).

FABLRMS (3:1 mixture of dithiothreitol and dithioerythritol in MeOH) m/e 321 g/mole ($M^++H$, $C_{17}H_{21}N_2O_2Cl$= 320.8 g/mole.)

HPLC (Vydac; C18; diameter=4.6 mm; length=15 cm; gradient=$CH_3CN$ [0.1% TFA]-$H_2O$ [0.1% TFA], 5%–95%, 95–5% over 20 min. 1.5 ml/min flow rate; RT=11.70 min; focus=215 nm; 97.4% pure.

EXAMPLE 5

4-(2-Chlorophenyl)-4-cyanopiperidine Hydrochloride

A solution of EtOAc saturated with HCl (200 ml) was added to 4-(2-chlorophenyl)-4-cyano-N-(1,1-dimethylethoxycarbonyl)piperidine, (880 mg, 2.74 mmol). The resulting mixture was allowed to react for 1 hour at room temperature. The EtOAc was removed in vacuo affording 4-(2-Chlorophenyl)-4-cyanopiperidine hydrochloride as a white solid.

$^1$H NMR ($CD_3OD$, 400 MHz) d 7.53 (dd, 1H, J=2.0, 4.3 Hz), 7.5 (dd, 1H, J=2.0, 5.3 Hz), 7.40 (ddd, 2H, J=2.0, 6.0, 7.9 Hz), 3.14 (ddd, 4H, J=2.2, 10.8, 12.4 Hz), 2.51 (dd, 2H, J=2.2, 13.5 Hz), 2.00 (dt, 2H, J=3.4, 13.5 Hz).

FABLRMS (3:1 mixture of dithiothreitol and dithioerythritol in MeOH) m/e 221 g/mole ($M^++H$, C13H16N2=220.7 g/mole.)

HPLC (Vydac; C18; diameter=4.6 mm; length=15 cm; gradient=$CH_3CN$ [0.1% TFA]-$H_2O$ [0.1% TFA], 5%–95%, 95–5% over 20 min. 1.5 ml/min flow rate; RT=5.744 min; focus=215 nm; 99.04% pure.

Anal. Calcd for $C_{12}H_{13}N_2Cl$. HCl and 0.60 $H_2O$: C=62.26, H=6.18, N=12.10. Found: C=62.29, H=5.69, N=11.71.

EXAMPLE 6

4-(2-Chlorophenyl)-4-cyano-N-(3-[N-{1,1-dimethylethoxycarbonyl}]amino)propylpiperidine A solution of 4-(2-chlorophenyl)-4-cyanopiperidine hydrochloride (1 g, 3.90 mmol) and N-(3-bromopropyl)-N-(1,1-dimethylethoxy)carbonyl amine (924.3 mg, 3.90 mmol) in DMF (2 mL) was treated with N,N-diisopropylethylamine (5.056 ml, 29.64 mmole) at room temperature (2 d). The solvent was removed in vacuo, the residue dissolved in EtOAc (100 ml) and washed with saturated NaHCO$_3$ (30 ml), H$_2$O (2×30ml), and saturated aqueous NaCl (30 ml), dried (Na$_2$SO$_4$) and concentrated in vacuo. PCTLC (SiO$_2$, 6 mm, 10% MeOH; 90% CH$_2$Cl$_2$) afforded 4-(2-chlorophenyl)-4-cyano-N-[3-{N-(1,1-dimethyl-ethoxy) carbonyl}amino]propyl piperidine as an oil.

$^1$H NMR (CDCl$_3$, 400 MHz) d 7.53 (dd, 1H, J=1.7, 4.3 Hz), 7.51 (dd, 1H, J=2.1, 5.8 Hz), 7.40 (m, 2H), 3.11 (m, 4H), 2.54 (m, 6H), 2.11 (dd, 2H, J=2.0, 13.2 Hz), 1.72 (br t, 2H, J=6.5 Hz), 1.44 (s, 9H)

HPLC (Vydac; C18; diameter=4.6 mm; length=15 cm; gradient=CH$_3$CN [0.1% TFA]-H$_2$O [0.1% TFA], 5%–95%, 95–5% over 20 min. 1.5 ml/min flow rate; RT=7.935 min; focus=215 nm; 93.76% pure.

EXAMPLE 7

N-(3-amino)propyl-4-(2-chlorophenyl)-4-cyanopiperidine Dihydrochloride

A solution of saturated HCl-EtOAc (200 ml) was added to 4-(2-Chlorophenyl)-4-cyano-N-(3-[N-{1,1-dimethylethoxycarbonyl}]amino)propylpiperidine (1.12 mg, 3.0 mmol). The resulting mixture was allowed to react for 1 hour at room temperature. The EtOAc was removed in vacuo affording 4-(2-chlorophenyl)-4-cyano-N-(3-amino) propyl-piperidine dihydrochloride as a white solid.

$^1$H NMR (CD$_3$OD, 400 MHz) d 7.57 (m, 2H), 7.46 (m, 2H), 3.89 (d br d, 2H, J=12.9 Hz), 3.43 (m, 4H), 3.1 (br dt, 2H, J=7.7 Hz), 2.93 (br d, 2H, J=15.4 Hz), 2.55 (br dt, 2H), 2.22 (m, 2H).

HPLC (Vydac; C18; diameter=4.6 mm; length=15 cm; gradient=CH$_3$CN [0.1% TFA]-H$_2$O [0.1% TFA], 5%–95%, 95–5% over 20 min. 1.5 ml/min flow rate; RT=5.36 min; focus=215 nm; 95.5% pure.

EXAMPLE 8

4-Cyano-N-(3-[N-{1,1-dimethylethoxycarbonyl}] amino)4-(2-methylphenyl)propylpiperidine A solution of 4-cyano-4-(2-methylphenyl) piperidine hydrochloride (1 g, 4.22 mmol) and N-(3-bromopropyl)-N-(1,1-dimethylethoxy)carbonyl amine (1.1 g, 4.65 mmol) in DMF (2 mL) was treated with N,N-diisopropylethylamine (5.5 ml, 32.07 mmole) at room temperature (4 d). The solvent was removed in vacuo, the residue was dissolved in EtOAc (100 ml) and washed with saturated NaHCO$_3$ (30 ml), H$_2$O (2×30ml), and saturated aqueous NaCl (30 ml), dried (Na$_2$SO$_4$) and concentrated in vacuo. PCTLC (SiO$_2$, 6 mm, 10% MeOH; 90% CH$_2$Cl$_2$) afforded 4-cyano-4-(2-methylphenyl)-N-[3-{(1,1-dimethyl-ethoxy) carbonyl}amino]propyl piperidine as an oil.

$^1$H NMR (CDCl$_3$, 400 MHz) d 7.26 (m, 4H), 3.22 (d, 2H, J=6.0 Hz), 3.05 (br d, 2H, J=12.2 Hz), 2.65 (s, 3H), 2.54 (m, 4H), 2.31 (br dd, 2H, J=13.4 Hz), 2.06 (br dt, 2H, J=12.2 Hz), 1.71 (t, 2H, J=6.0 Hz), 1.44 (s, 9H).

FABLRMS (3:1 mixture of dithiothreitol and dithioerythritol in MeOH) m/e 358 g/mole (M$^+$+H, C$_{25}$H$_{29}$N$_2$O$_5$SCl= 357.6 g/mole.)

HPLC (Vydac; C18; diameter=4.6 mm; length=15 cm; gradient=CH$_3$CN [0.1% TFA]-H$_2$O [0.1% TFA], 5%–95%, 95–5% over 20 min. 1.5 ml/min flow rate; RT=7.982 min; focus=215 nm; 96.50% pure.

EXAMPLE 9

N-(3-Amino)propyl-4-cyano-4-(2-methylphenyl) piperidine Dihydrochloride

A solution of EtOAc saturated with HCl (200 ml) was added to 4-cyano-N-(3-[N-{1,1-dimethylethoxycarbonyl}] amino)4-(2-methylphenyl)propylpiperidine (900 mg, 2.51 mmol). The resulting mixture was allowed to react room temperature (1 h). The EtOAc was removed in vacuo affording 4-cyano-4-(2-methylphenyl)-N-(3-amino) propyl-piperidine dihydrochloride as a white solid.

$^1$H NMR (CD$_3$OD, 400 MHz) d 7.35 (m, 4H), 3.87 (br d, 2H, J=12.5 Hz), 3.41 (m,4H), 3.11 (t, 2H, J=7.7 Hz), 2.74 (br dd, 2H, J=14.1 Hz), 2.66 (s, 3H), 2.51 (m, 2H), 2.23 (m, 2H)

HPLC (Vydac; C18; diameter=4.6 mm; length=15 cm; gradient=CH$_3$CN [0.1% TFA]-H$_2$O [0.1% TFA], 5%–95%, 95–5% over 20 min. 1.5 ml/min flow rate; RT=5.367 min; focus=215 nm; 95.96% pure).

EXAMPLE 10

2,2-Bis(4-chlorophenyl)-N-[3-(4-cyano-4-{2-methylphenyl}piperidin-1-yl)propyl]acetamide A solution of N-(3-amino)propyl-4-cyano-4-(2-methylphenyl)piperidine dihydrochloride (150 mg, 0.612 mmol) and 2,2-bis(4-chlorophenyl) acetic acid (169.62 mg, 0.612 mmol) in DMF (1 mL) was treated with 1-(3-dimethylaminopropyl)-3-ethylcarbodimide hydrochloride (EDCI), (131.41 mg, 0.685 mmol), 1-hydroxy benzotriazole hydrate (HOBt), (95.26 mg, 0.685 mmole), and NaHCO$_3$ (257.04 mg, 3.06 mmol) at room temperature (18 h). The solvent was removed in vacuo, the residue was dissolved in EtOAc (200 ml) and washed with saturated NaHCO$_3$ (50 ml), H$_2$O (2×50 ml), and saturated aqueous NaCl (50 ml), dried (Na$_2$SO$_4$) and concentrated in vacuo. PCTLC (SiO$_2$, 4 mm, 1:1 hexane: EtOAc) afforded N-[4-cyano-4-(2-methylphenyl)piperidin-1-yl)propyl]-2-[bis (4-chlorophenyl)]acetamide as a white powder.

$^1$H NMR (CD$_3$OD, 400 MHz) d 7.30 (m, 12H), 4.93 (s, 1H), 3.30 (m, 2H), 2.61 (s, 3H), 2.45 (m, 4H), 2.33 (d br d, 2H, J=11.7 Hz), 1.98 (d d, 2H, J=9.8 Hz, 2.4 Hz), 1.74 (t, 2H, J=7.3 Hz).

FABLRMS (3:1 mixture of dithiothreitol and dithioerythritol in MeOH) m/e 520 g/mole (M$^+$+H, C$_{30}$H$_{31}$N$_3$OCl$_2$= 520.5 g/mole.)

HPLC (Vydac; C18; diameter=4.6 mm; length=15 cm; gradient=CH$_3$CN [0.1% TFA]-H$_2$O [0.1% TFA], 5%–95%, 95–5% over 20 min. 1.5 ml/min flow rate; RT=10.74 min; focus=215 nm; 98.1% pure.

Anal. Calcd for C$_{30}$H$_{31}$N$_3$OCl$_2$ and 0.90 H$_2$O: C=67.14, H=6.16, N=7.83. Found: C=67.14, H=5.87, N=8.04.

EXAMPLE 11

2,2-Bis(4-chlorophenyl)-N-[3-(4-{2-chlorophenyl}4-cyanopiperidin-1-yl)propylacetamide A solution of N-(3-amino)propyl-4-(2-chlorophenyl)-4-cyanopiperidine dihydrochloride (248.8 mg, 0.711 mmol) and 2,2-bis(4-chlorophenyl) acetic acid (200 mg, 0.711 mmol) in DMF (1 mL) was treated with 1-(3-dimethylaminopropyl)-3-ethylcarbodimide hydrochloride, (EDCI), (205.1 mg, 1.07 mmol), 1-hydroxybenzotriazole hydrate, (HOBt), (148.7 mg, 1.07 mmole), and NaHCO$_3$ (298.62 mg, 3.55 mmol) at room temperature (18 h). The solvent was removed in vacuo, the residue dissolved in EtOAc (200 ml) and washed with saturated NaHCO$_3$ (50 ml), H$_2$O (2×50 ml), and saturated aqueous NaCl (50 ml), dried (Na$_2$SO$_4$) and concentrated in vacuo. PCTLC (SiO$_2$, 4 mm, 1:1 hexane: EtOAc) afforded N-[4-(2-chlorophenyl)-4-cyanopiperidin-1-yl)propyl]-2-[bis(4-chlorophenyl)] acetamide as a white powder.

¹H NMR (CD₃OD, 400 MHz) d 7.51 (m, 2H), 7.40 (m, 2H), 7.30 (d d, 8H, J=7.5 Hz, 15.5 Hz), 4.93 (s, 1H), 3.21 (d, 2H, J=11.9 Hz), 3.02 (d, 2H, J=11.9), 2.48 (m, 6H), 2.01 (t, 2H, J=12.5 Hz), 1.74 (t, 2H, J=7.2 Hz),

FABLRMS (3:1 mixture of dithiothreitol and dithioerythritol in MeOH) m/e 542 g/mole (M⁺+H, $C_{29}H_{28}N_3O_1Cl_3$= 541.9 g/mole.)

HPLC (Vydac; C18; diameter=4.6 mm; length=15 cm; gradient=CH₃CN [0.1% TFA]-H₂O [0.1% TFA], 5%–95%, 95–5% over 20 min. 1.5 ml/min flow rate; RT=10.68 min; focus=215 nm; 99.8% pure.

Anal. Calcd for $C_{29}H_{28}N_3OCl_3$ and 0.60 H₂O: C=63.13, H=5.33, N=7.62. Found: C=63.16, H=5.16, N=7.62.

EXAMPLE 12

2,2-Bis(4-methylphenyl)-N-[3-(4-cyano-4-{2-methylphenyl}piperidin-1-yl)propyl]acetamide A solution of 4-cyano-4-(2-methylphenyl)piperidine hydrochloride (200 mg, 0.845 mmol) and N-(3-bromopropyl)-2,2-bis(4-methylphenyl)carboxamide (365.35 mg, 1.014 mmol) in DMF (2 mL) was treated with N,N-diisopropylethylamine (0.588 ml, 6.42 mmol) at room temperature (18 h). The solvent was removed in vacuo, and the residue dissolved in EtOAc (200 ml) and washed with saturated NaHCO₃ (50 ml), H₂O (2×50 ml), and saturated aqueous NaCl (50 ml), dried (Na₂SO₄) and concentrated in vacuo. PCTLC (SiO₂, 4 mm, 1:1 hexane: EtOAc) afforded N-[4-cyano-4-(2-methylphenyl)piperidin-1-yl) propyl]-2-[bis(4-methyl-phenyl)]acetamide (200 mg, 487 mg theoretical, 41%) as a white powder.

¹H NMR (CD₃OD, 400 MHz) d 7.34 (d, 1H, J=1.5 Hz), 7.32 (t, 3H, J=1.8 Hz), 7.18 (m, 8H), 4.86 (s, 1H), 3.28 (d, 2H, J=6.6 Hz), 3.00 (br dd, 2H, J=12.8 Hz), 2.61 (s, 3H), 2.43 (m, 4H), 2.31 (m, 2H), 2.29 (s, 6H), 1.96 (dt, 2H, J=9.7 Hz, 2.4 Hz), 1.74 (m, 2H).

FABLRMS (3:1 mixture of dithiothreitol and dithioerythritol in MeOH) m/e 480 g/mole (M⁺+H, $C_{32}H_{37}N_3O_1Cl_3$= 480.1 g/mole.)

HPLC (Vydac; C18; diameter=4.6 mm; length=15 cm; gradient=CH₃CN [0.1% TFA]-H₂O [0.1% TFA], 5%–95%, 95–5% over 20 min. 1.5 ml/min flow rate; RT=10.58 min; focus=215 nm; 97.0% pure.

Anal. Calcd for $C_{32}H_{37}N_3O$ and 0.40 H₂O: C=78.94, H=7.83 N=8.63. Found: C=78.98, H=7.71, N=8.69.

EXAMPLE 13

2,2-Bis(4-methylphenyl)-N-[3-(4-{2-chlorophenyl}4-cyanopiperidine-1-yl)propyl] acetamide A solution of 4-(2-chlorophenyl)-4-cyano-piperidine (200 mg, 0.910 mmol) and N-(3-bromopropyl)-2,2-di-(4-methylphenyl)carboxamide (36.24 mg, 1.092 mmol) in DMF (2 mL) was stirred for 18 hours. The solvent was removed in vacuo, the residue dissolved in EtOAc (200 ml) and washed with saturated NaHCO₃ (50 ml), H₂O (2×50ml), and saturated aqueous NaCl (50 ml), dried (Na₂SO₄) and concentrated in vacuo. PCTLC (SiO₂, 4 mm, 1:1 hexane:EtOAc) afforded N-[4-(2-chlorophenyl)-4-cyano-piperidin-1-yl)propyl]-2-[bis(4-methyl-phenyl)]-acetamide as a white powder.

¹H NMR (CDCl₃, 400 MHz: d 7.53 (ddd, 1H, J=1.8, 2.8, 3.0 Hz), 7.33 (t, 3H, J=2.2 Hz), 7.14 (d, 4H, J=8.1 Hz), 7.08 (d, 4H, J=8.1 Hz), 4.83 (s, 1H), 3.42 (dd, 2H, J=1.5, 4.8 Hz), 3.05 (br d, 2H), 2.59 (br m, 4H), 2.46 (br dd, 2H, J=13.2 Hz), 2.29 (s, 6H), 2.02 (br m, 2H), 1.74 (br t, 2H).

FABLRMS (3:1 mixture of dithiothreitol and dithioerythritol in MeOH) m/e 500 g/mole (M⁺+H, $C_{31}H_{34}N_3O_1Cl_1$= 500.1 g/mole.)

HPLC (Vydac; C18; diameter=4.6 mm; length=15 cm; gradient=CH₃CN [0.1% TFA]-H₂O [0.1% TFA], 5%–95%, 95–5% over 20 min. 1.5 ml/min flow rate; RT=10.339 min; focus=215 nm; 99.7% pure.

Anal. Calcd for $C_{31}H_{34}N_3O_1Cl$ and 0.65 H₂O: C=72.75 H=6.95 N=8.21 Found: C=72.75, H=6.84, N=8.21.

EXAMPLE 14

2,2-Bis(4-methylphenyl)-N-[3-({4-carboxymethyl}4-phenylpiperidin-1-yl)propyl] acetamide Hydrochloride A solution of 3-amino-N-(4-carboxymethyl-4-phenyl) propylpiperidine dihydrochloride (139.41 mg, 0.416 mmol) and 2,2, di(4-methylphenyl) acetic acid (100 mg, 0.416 mmol) in DMF (1 mL) was treated with 1-(3-dimethylaminopropyl)-3-ethylcarbodimide hydrochloride, (EDCI), (119.7 mg, 0.624 mmol), 1-hydroxy benzotriazole hydrate, (HOBt), (86.72 mg, 0.624 mmole), and NaHCO₃ (34.95 mg, 0.416 mmol) at room temperature (18 h). The solvent was removed in vacuo, the residue dissolved in EtOAc (200 ml) and washed with saturated NaHCO₃ (50 ml), H₂O (2×50 ml), and saturated aqueous NaCl (50 ml), dried (Na₂SO₄) and concentrated in vacuo. PCTLC (SiO₂, 4 mm, 10% MeOH: 90% CH₂Cl₂) afforded N-[4-carboxyethyl-4-phenyl)piperidin-1-yl) propyl]-2-[bis(4-methylphenyl)]acetamide as a white powder.

¹H NMR (CD₃OD, 400 MHz) d 7.35 (m, 3H), 7.25 (m, 1H), 7.11 (m, 8H), 4.93 (s, 1H), 3.63 (s, 3H), 3.26 (m,2H), 2.77 (m, 2H), 2.52 (br d, 2H, 12.3 Hz), 2.30 (s, 6H), 2.28 (br d, 2H, 12.3 Hz), 2.18 (t, 2H, 7.3 Hz), 1.98 (br t, 2H), 1.74 (t, 2H, J=7.3 Hz).

FABLRMS (3:1 mixture of dithiothreitol and dithioerythritol in MeOH) m/e 499 g/mole (M⁺+H, $C_{32}H_{38}N_2O_3$=498.7 g/mole.)

HPLC (Vydac; C18; diameter=4.6 mm; length=15 cm; gradient=CH₃CN [0.1% TFA]-H₂O [0.1% TFA], 5%–95%, 95–5% over 20 min. 1.5 ml/min flow rate; RT=8.66 min; focus=215 nm; 99.2% pure).

Anal. Calcd for $C_{32}H_{39}N_2O_3Cl_1$ and 0.05 H₂O and 0.25 CH₂Cl₂: C=69.51, H=7.16, N=5.03. Found: C=69.53, H=6.91, N=5.22.

EXAMPLE 15

2,2-Bis(4-chlorophenyl)-N-[3-(4-cyano-4-phenylpiperidin-1-yl)propylacetamide

A solution of 4-cyano-4-phenyl-N-(3-amino) propylpiperidine dihydrochloride (104.5 mg, 0.3557 mmol, 1.2 equiv) and 2,2-bis(4-chlorophenyl) acetic acid (100.0 mg, 0.3557 mmol, 1.0 equiv) in anhydrous DMF (1.5 mL) at 25° C. was treated with EDCI (82 mg, 0.42684 mmol, 1.2 equiv), HOBt (58 mg, 0.42684 mmol, 1.2 equiv), and NaHCO₃ (150 mg, 1.7785 mmol, 5 equiv) under Ar. The resulting mixture was stirred at 25° C. (24 h) and quenched by the addition of H₂O (15 mL) and CH₂Cl₂ (10 mL). The aqueous phase was extracted with CH₂Cl₂ (2×10 mL) and the combined organic extracts were washed with H₂O (2×15 mL) and saturated aqueous NaCl (1×15 mL), dried (Na₂SO₄), and concentrated in vacuo affording a white foam which solidified upon standing. PCTLC (SiO$_2$, 2 mm, 0–10% CH$_3$OH—CH$_2$Cl$_2$ afforded the desired product.

$^1$H NMR (CD$_3$OD, 400 MHz) d 7.4–7.6 (m, 5H), 7.25–7.40 (m, 8H), 4.99 (s, 1H), 3.70 (br s, 2H), 3.37 (br m, 3H), 3.21 (br m, 3H), 2.48 (br d, 2H, J=13.5 Hz), 2.35 (br m, 2H), 2.02 (br m, 2H).

HPLC (Vydac; C18; diameter=4.6 mm; length=15 cm; gradient=CH$_3$CN [0.1% TFA]-H$_2$O [0.1% TFA], 5%–95%, 95–5% over 20 min. 1.5 ml/min flow rate; RT=10.66 min; focus=215 nm; 97.6% pure).

Anal. Calcd for C$_{29}$H$_{29}$N$_3$OCl$_2$·HCl and 0.55 DMF and 0.85 CH$_2$Cl$_2$: C=57.73, H=5.47, N=7.57. Found: C=57.82, H=5.46, N=7.66.

EXAMPLE 16

2,2-Bis(4-methylphenyl)-N-[3-(4-cyano-4-phenylpiperidin-1-yl)propyl]acetamide Hydrochloride A solution of 4-cyano-4-phenyl piperidine hydrochloride (100 mg, 0.449 mmol, 1.0 equiv) in anhydrous/degassed DMF (1.0 mL) at 25° C. was treated with N-(3-bromopropyl)-2,2-di-(4-methylphenyl)carboxamide (178 mg, 0.449 mmol, 1.1 equiv), and iPr$_2$NEt (157 µL, 0.9878 mmol, 2.2 equiv) under Ar. The resulting mixture was stirred at 25° C. (24 h) and quenched by the addition of saturated aqueous NaHCO$_3$ (5.0 mL) and CH$_2$Cl$_2$ (5.0 mL). The aqueous phase was extracted with CH$_2$Cl$_2$ (2×5.0 mL) and the combined organic extracts were washed with water (3×10 mL) and saturated aqueous NaCl (1×10 mL), dried (Na$_2$SO$_4$), and concentrated in vacuo. Chromatography (PCTLC, SiO$_2$, 2 mm, 0–10% CH$_3$OH—CH$_2$Cl$_2$) afforded the alkylated product, which was concentrated in vacuo, dissolved in dry EtOAc (2.0 mL), cooled to 0° C. and treated with saturated HCl-EtOAc (5 mL), concentrated in vacuo after ~1 h, triturated with dry ether (3×2.0 mL) and thoroughly dried.

$^1$H NMR (CDCl$_3$, 400 MHz) d 7.41–7.47 (m, 3H), 7.37 (m, 2H), 7.11 (m, 8H) 6.40 (br s, 1H), 4.82 (s, 1H), 3.38 (dd, 2H, J=5.9, 12.3 Hz), 2.93 (br m, 2H), 2.45 (br m, 4H), 2.29 (s, 6H, 2.04 (br dd, 2H, J=12.4 Hz), 1.93 (br m, 2H), 1.72 (br m, 2H).

HPLC (Vydac; C18; diameter=4.6 mm; length=15 cm; gradient=CH$_3$CN [0.1% TFA]-H$_2$O [0.1% TFA], 5%–95%, 95–5% over 20 min. 1.5 ml/min flow rate; RT=9.86 min; focus=215 nm; 98.2% pure).

Anal. Calcd for C$_{31}$H$_{35}$N$_3$O·HCl: C=74.15, H=7.23, N=8.37 Found: C=74.18, H=7.23, N=8.03.

EXAMPLE 17

As a specific embodiment of an oral composition, 100 mg of the compound of Example 12 is formulated with sufficient finely divided lactose to provide a total amount of 580 to 590 mg to fill a size O hard gel capsule.

EXAMPLE 18

Screening Assay: Alpha 1a Adrenergic Receptor Binding

Membranes prepared from the stably transfected human $\alpha_{1a}$ cell line (ATCC CRL 11140) were used to identify compounds that bind to the hums alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from the $\alpha_{1a}$ cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values ≦50 nM.

EXAMPLE 19

Selective Binding Assays

Membranes prepared from stably transfected human $a_{1d}$ and $\alpha_{1b}$ cell lines (ATCC CRL 11138 and CRL 11139, respectively) were used to identify compounds that selectively bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 20

Exemplary Counterscreens

1. Assay Title: Dopamine D2, D3, D4 in vitro screen

Objective of the Assay

The objective of this assay is to eliminate agents which specifically affect binding of [3H] spiperone to cells expressing human dopamine receptors D2, D3 or D4.

Method

Modified from VanTol et al (1991); Nature (Vol 350) Pg 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 µg membranes in a total volume of 500 µl containing 0.2 nM [3H]-spiperone. Non-specific binding is defined using 10 µM apomorphine. The assay is terminated after a 2 hour incubation at room temperature by rapid filtration over GF/B filters presoaked in 0.3% PEI, using 50mM Tris-HCl pH 7.4.

2. Assay Title: Serotonin 5HT1a

Objective of the Assay

The objective of this assay is to eliminate agents which specifically affect binding to cloned human 5HT1a receptor Method Modified from Schelegel and Peroutka *Biochemical Pharmacology* 35:1943–1949 (1986).

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000 Xg for 30', and then the supernatant is centrifuged again at 38,000 Xg for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 µM propranolol. The assay is terminated after a 1 hour incubation at room temperature by rapid filtration over GF/C filters

EXAMPLE 21

Exemplary Functional Assays

In order to confirm the specificity of compounds for the human alpha 1a adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 µM (for rat), 10 µM (for dog) and 20 µM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ (-log $K_b$) values were obtained from Schild plot when three or more concentrations were tested. When less than three concentrations of antagonist are tested, $K_b$ values are calculated according to the following formula $$K_b = \frac{[B]}{x-1},$$

where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha-1 receptor antagonists which also have pronounced vascular effects. Because we have identified the alpha-1a receptor subtype as the predominant subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha-1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha-1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha-1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula:

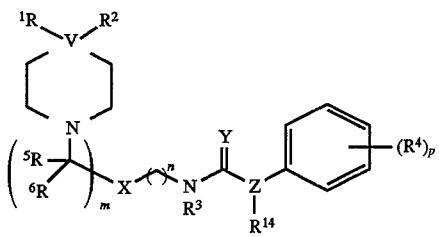

wherein

V is selected from carbon or nitrogen, provided that when V is nitrogen, then $R^2$ is absent;

X is selected from $CH_2$, $CHOR^5$, CHF, $CHR^5$, $CR^5R^6$, $CF_2$, $CHCHF_2$, V is carbon;

Z is selected from CH, $CCO_2R^5$, $C(CH_2)_qCO_2(R^5)_2$, $COR^{12}$, $CNR^{12}R^{13}$, $COR^{12}$, $CNR^{12}R^{13}$, $C(CH_2)_qCH_2N(R^5)_2$;

$R^1$ is selected from unsubstituted, mono- or poly-substituted phenyl where the substituents on the phenyl are independently selected from halogen, cyano, $CO_2R^5$, $OR^5$, $(CH_2)_qCON(R^5)_2$, $(CH_2)_qCO_2R^5$ or $C_{1-4}$ alkyl; or unsubstituted, mono- or poly-substituted pyridyl, thiophenyl, furanyl or naphthyl where the substituents on the pyridyl, thiophenyl, furanyl or naphthyl are independently selected from $CF_3$, phenyl, $OR^5$, halogen, $C_{1-4}$ alkyl or $C_{3-8}$ cycloalkyl;

$R^2$ is selected from cyano, $CO_2R^5$, $CON(R^5)_2$, tetrazole or isooxadiazole;

$R^3$ is selected from hydrogen, cyano, $CO_2R^5$, $CON(R^5)_2$, $C_{1-8}$ alkyl, $C_{3-8}$ cycloalkyl or $(CH_2)_qCO_2R^5$;

$R^4$ is selected from hydrogen, $OR^5$, $C_{1-8}$ alkyl or halogen;

$R^5$ and $R^6$ are each independently selected from hydrogen, $C_{1-8}$ alkyl, $C_{3-8}$ cycloalkyl, halogen substituted $C_{1-4}$ alkyl and halogen substituted $C_{3-8}$ cycloalkyl;

$R^8$ is selected from hydrogen, cyano or $SO_2R^5$;

$R^{12}$ and $R^{13}$ are each independently selected from hydrogen, $C_{1-8}$ alkyl, $C_{3-8}$ cycloalkyl, CHO, $COR^5$, $CONR^5R^6$, $(CH_2)_qOR^5$, $R^{14}$ is selected from hydrogen, $C_{1-8}$ alkyl, $C_{3-8}$ cycloalkyl, $C_{1-4}$ alkoxy, morpholinyl, piperazinyl, δ-valerolactamyl, 2-pyrrolidonyl, thiophenyl, furanyl, pyridinyl, naphthyl or unsubstituted, mono- or poly-substituted phenyl where the substituents on the phenyl are independently selected from $C_{1-4}$ alkyl, $OR^5$ or halogen;

m, n and q are each independently an integer of from zero to three, provided that when m and n are both zero, then X is selected from $CH_2$, CHF, $CHR^5$, $CR^5R^6$, $CF_2$, $CHCHF_2$, $C=CF_2$ or C=O; and p is an integer of from zero to five;

and the pharmaceutically acceptable salts thereof.

2. The compound of claim 1, of the formula

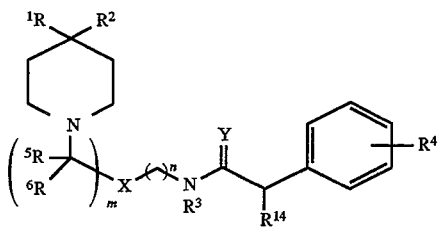

wherein $R^1$ is selected from unsubstituted, mono- or poly-substituted phenyl where the substitutents on the phenyl are independently selected from halogen, cyano, $CO_2R^5$, $OR^5$, $CON(R^5)_2$ or $C_{1-4}$ alkyl; pyridyl; thiophenyl; furanyl; or unsubstituted, mono- or poly-substituted naphthyl where the substituent on the naphthyl are independently selected from $CF_3$, phenyl, $OR^5$, halogen, $C_{1-4}$ alkyl or $C_{3-8}$ cycloalkyl;

and the pharmaceutically acceptable salts thereof.

3. The compound of claim 2, of the formula

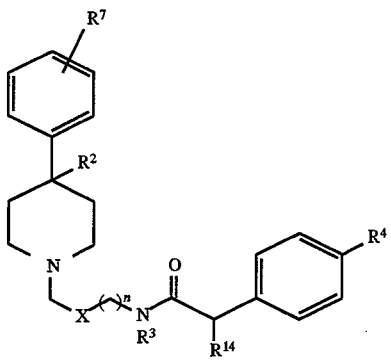

wherein $R^2$ is selected from cyano or $CO_2R^5$;

$R^4$ is selected from hydrogen, halogen or $C_{1-4}$ alkyl;

$R^7$ is selected from hydrogen, $CF_3$, cyano, halogen or $C_{1-4}$ alkyl;

$R^{14}$ is selected from hydrogen, $C_{1-8}$ alkyl, $C_{3-8}$ cycloalkyl or unsubstituted, mono- or poly-substituted phenyl where the substitutent on the phenyl are independently selected from halogen or $C_{1-4}$ alkyl;

and the pharmaceutically acceptable salts thereof.

4. The compound of claim 3, of the formula

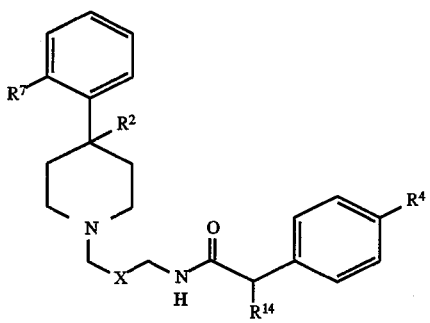

wherein $R^{14}$ is selected from $C_{3-8}$ cycloalkyl or unsubstituted or mono-substituted phenyl wherein the substituent is selected from halogen or $C_{1-4}$ alkyl;

and the pharmaceutically acceptable salts thereof.

5. The compound of claim 4, wherein

X is selected from $CH_2$, CHOH or C=O;

$R^2$ is selected from cyano or $CO_2CH_3$;

$R^4$ is selected from hydrogen, chloro or methyl;

$R^7$ is selected from hydrogen, chloro or methyl; and $R^{14}$ is selected from cyclopentyl, cyclohexyl, phenyl, p-tolyl or p-chlorophenyl;

and the pharmaceutically acceptable salts thereof.

6. The compound of claim 5 selected from 2,2-Bis(4-chlorophenyl)-N-[3-(4-cyano-4-phenylpiperidin-1-yl)propyl]acetamide;

2,2-Bis(4-chlorophenyl)-N-[3-(4-cyano-4-{2-methylphenyl}piperidin-1-yl)propyl]acetamide;

2,2-Bis(4-chlorophenyl)-N-[3-(4-{2-chlorophenyl}4-cyanopiperidin-1-yl)propyl]acetamide;

2,2-Bis(4-methylphenyl)-N-[3-(4-cyano-4-phenylpiperidin-1-yl)propyl]acetamide hydrochloride;

2,2-Bis(4-methylphenyl)-N-[3-({4-carboxymethyl}4-phenylpiperidin-1-yl)propyl]acetamide hydrochloride;

2,2-Bis(4-methylphenyl)-N-[3-(4-cyano-4-{2-methylphenyl}piperidin-1-yl)propyl]acetamide;

2,2-Bis(4-methylphenyl)-N-[3-(4-{2-chlorophenyl}4-cyanopiperidine-1-yl)propyl]acetamide;

2,2-Bis(4-methylphenyl)-N-[3-(4-cyano-4-phenylpiperidin-1-yl)2-hydroxypropyl]acetamide;

2,2-Bis(4-methylphenyl)-N-[3-(4-cyano-4-{2-methylphenyl}piperidin-1-yl)2-hydroxypropyl]acetamide;

2,2-Bis(4-methylphenyl)-N-[3-(4-cyano-4-phenylpiperidine-1-yl)2-oxopropyl]acetamide; or 2,2-Bis(4-methylphenyl)-N-[3-(4-cyano-4-{2-methylphenyl}piperidin-1-yl)2-oxopropyl]acetamide; or and the pharmaceutically acceptable salts thereof.

7. A pharmaceutical composition comprising a therapeutically effective amount of the compound of claim 1 and a pharmaceutically acceptable carrier.

8. The composition of claim 7 further comprising a therapeutically effective amount of a testosterone 5-alpha reductase inhibitor.

9. The composition of claim 8, wherein the testosterone 5-alpha reductase inhibitor is a type 1, a type 2, both a type 1 and a type 2 or a dual type 1 and type 2 testosterone 5-alpha reductase inhibitor.

10. The composition of claim 9, whereto the testosterone 5-alpha reductase inhibitor is a type 2 testosterone 5-alpha reductase inhibitor.

11. The composition of claim 10, wherein the testosterone 5-alpha reductase inhibitor is finasteride.

12. A method of treating benign prostatic hyperplasia in a subject in need thereof which comprises administering to the subject a therapeutically effective amount of the compound of claim 1.

13. The method of claim 12, wherein the compound additionally does not cause a fall in blood pressure at dosages effective to alleviate benign prostatic hypertophy.

14. The method of claim 12, wherein the compound is administered in combination with a testosterone 5-alpha reductase inhibitor.

15. The method of claim 14, whereto the testosterone 5-alpha reductase inhibitor is finasteride.

16. A method of treating benign prostatic hyperplasia in a subject in need thereof which comprises administering a therapeutically effective amount of the composition of claim 7.

17. The method of claim 16, wherein the composition further comprises a therapeutically effective amount of a testosterone 5-alpha reductase inhibitor.

18. A method of inhibiting contraction of prostate tissue in a subject in need thereof which comprises administering to the subject a therapeutically effective amount of the compound of claim 1.

19. The method of claim 18, wherein the compound additionally does not cause a fall in blood pressure at dosages effective to inhibit contraction of prostate tissue.

20. The method of claim 18, wherein the compound is administered in combination with a testosterone 5-alpha reductase inhibitor.

21. The method of claim 20, wherein the testosterone 5-alpha reductase inhibitor is finasteride.

22. A method of treating a disease which is susceptible to treatment by antagonism of the alpha 1a receptor which comprises administering to a subject in need thereof an amount of the compound of claim 1 effective to treat the disease.

* * * * *

UNITED STATES PATENT AND TRADEMARK OFFICE
CERTIFICATE OF CORRECTION

PATENT NO. : 5,661,163

DATED : 8/26/97

INVENTOR(S) : Michael A. Patane, Mark G. Bock, Roger M. Freidinger and Rose Ann Ponticello It is certified that error appears in the above-identified patent and that said Letters Patent is hereby corrected as shown below:

In claim 1:

At column 31, lines 29-30, delete "V is selected from carbon or nitrogen, provided that when V is nitrogen, then $R^2$ is absent;" and substitute therefor -- V is carbon; --.

At column 31, line 33, delete "V is carbon;" and substitute therefor -- Y is selected from oxygen, $NR^8$ or sulfur; --.

Signed and Sealed this

Twenty-fourth Day of November, 1998

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,661,163
DATED : 8/26/97
INVENTOR(S) : Michael A. Patane, Mark G. Bock, Roger M. Freidinger and Rose Ann Ponticello It is certified that error appears in the above-identified patent and that said Letters Patent is hereby corrected as shown below:

In claim 1:

At column 31, line 32, after "$CHCHF_2$," insert -- $C=CF_2$ or $C=O$," --

Signed and Sealed this

Second Day of March, 1999

Attest:

Q. TODD DICKINSON

*Attesting Officer*   *Acting Commissioner of Patents and Trademarks*